(12) United States Patent
Delaney, Jr. et al.

(10) Patent No.: US 12,016,969 B2
(45) Date of Patent: Jun. 25, 2024

(54) INJECTABLE IN VIVO CROSSLINKING MATERIALS FOR USE AS SOFT TISSUE FILLERS

(71) Applicant: Boston Scientific Scimed, Inc., Maple Grove, MN (US)

(72) Inventors: Joseph T. Delaney, Jr., Minneapolis, MN (US); Mark W. Boden, Harrisville, RI (US); John Murphy, Cork (IE); Viktoria Molnar, Dungarvan (IE); Tatyana Dyndikova, Minneapolis, MN (US); Allison Zipp, Saint Michael, MN (US); Kolbein K Kolste, Boxboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 462 days.

(21) Appl. No.: 17/165,485

(22) Filed: Feb. 2, 2021

(65) Prior Publication Data
US 2021/0236690 A1 Aug. 5, 2021

Related U.S. Application Data

(60) Provisional application No. 62/969,863, filed on Feb. 4, 2020.

(51) Int. Cl.
*A61L 27/16* (2006.01)
*A61L 27/18* (2006.01)
(Continued)

(52) U.S. Cl.
CPC ............... *A61L 27/16* (2013.01); *A61L 27/18* (2013.01); *A61L 27/3839* (2013.01); *A61L 27/50* (2013.01)

(58) Field of Classification Search
CPC ..................................................... A61L 27/16
See application file for complete search history.

(56) References Cited

U.S. PATENT DOCUMENTS

| 6,818,018 B1 | 11/2004 | Sawhney |
| 10,272,164 B2 | 4/2019 | Campbell et al. |

(Continued)

FOREIGN PATENT DOCUMENTS

| CN | 101524560 A | 9/2009 | |
| EP | 2389925 A2 * | 11/2011 | ............. A61K 31/00 |

(Continued)

OTHER PUBLICATIONS

Alghoul, M., Codner, M. A. (2013). Retaining ligaments of the face: review of anatomy and clinical applications. Aesthetic surgery journal, 33(6), 769-782. https://doi.org/10.1177/1090820X13495405.

(Continued)

*Primary Examiner* — Michael F Pepitone
(74) *Attorney, Agent, or Firm* — Seager, Tufte & Wickhem LLP

(57) ABSTRACT

Described herein are injectable in vivo crosslinking materials for use as soft tissue filler comprising (a) a reactive multi-arm polymer that comprises a plurality of hydrophilic polymeric arms, at least a portion of the hydrophilic polymeric arms comprising one or more reactive end groups and (b) a multifunctional compound that comprises functional groups that are reactive with the reactive end groups of the reactive multi-arm polymer. Also described herein are systems and methods that are based on such materials.

18 Claims, 1 Drawing Sheet

(51) Int. Cl.
  *A61L 27/38* (2006.01)
  *A61L 27/50* (2006.01)

(56) References Cited

U.S. PATENT DOCUMENTS

| | | |
|---|---|---|
| 2008/0220047 A1 | 9/2008 | Sawhney et al. |
| 2011/0142936 A1 | 6/2011 | Campbell et al. |
| 2014/0072607 A1* | 3/2014 | Hedrick .................. A61P 31/04 525/461 |

FOREIGN PATENT DOCUMENTS

| | | | |
|---|---|---|---|
| EP | 2389925 A2 | 11/2011 | |
| WO | WO-2012057628 A2 * | 5/2012 | ............. A61K 47/50 |

OTHER PUBLICATIONS

International Search Report and Written Opinion for the International Patent Application No. PCT/US2021/016213, dated May 18, 2021, 10 pages.
"Augmenix Announces Positive Three-year SpaceOAR Clinical Trial Results," Imaging Technology News, Oct. 27, 2016.
"Augmenix Receives FDA Clearance to Market its TraceIT™ Tissue Marker," BusinessWire Jan. 28, 2013.

* cited by examiner

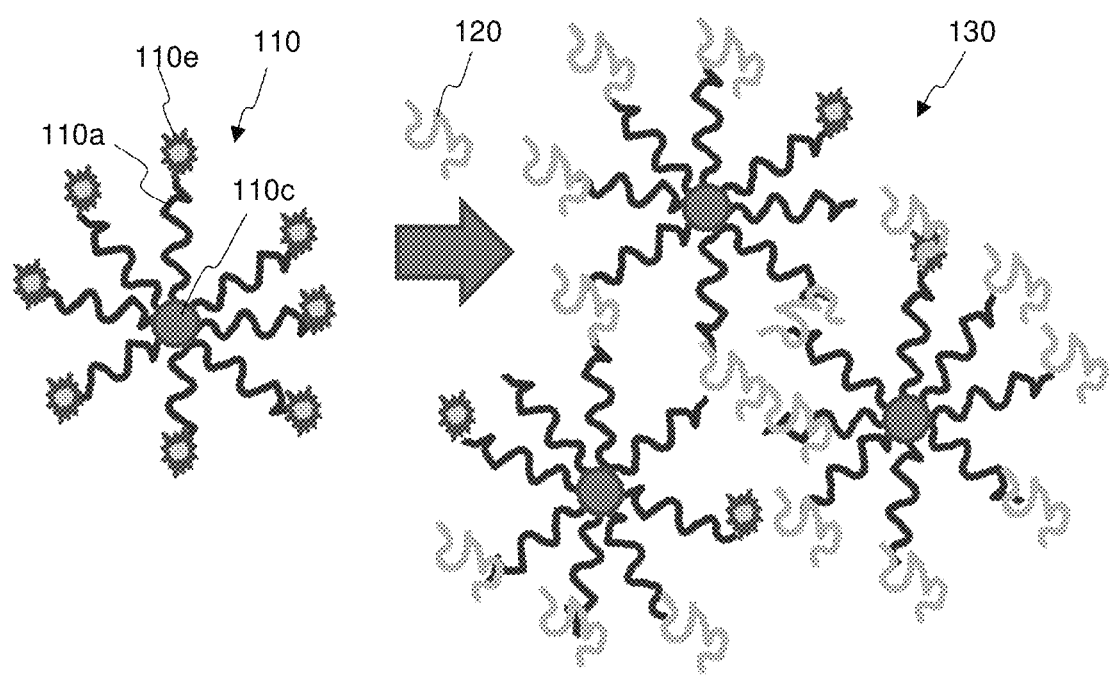

INJECTABLE IN VIVO CROSSLINKING MATERIALS FOR USE AS SOFT TISSUE FILLERS

CROSS-REFERENCE TO RELATED APPLICATIONS

The present application claims the benefit of U.S. Provisional Application Ser. No. 62/969,863, filed Feb. 4, 2020, the disclosure of which is herein incorporated herein by reference in its entirety.

FIELD

The present disclosure relates to soft-tissue fillers, to compositions for forming soft-tissue fillers, and to methods of administering soft-tissue fillers to patients.

BACKGROUND

Injectable soft-tissue fillers can provide a noninvasive option for reducing skin defects, such as wrinkles, lines, other volume loss due to the natural effects of aging, or scars, to enhance fullness of the lips or act as a spacer between skin and organs or between two organs.

The current standard of care for dermal fillers is based on hydrophilic biopolymers such as collagen or hyaluronic acid. Such biopolymers, while generally being well tolerated, cause allergic responses to them in some patients. In addition, biopolymers are also generally of high molecular weight, resulting in solutions having high intrinsic viscosity.

By employing non-biologically-derived hydrophilic polymers as an alternatives, there is potential for compositions having reduced immune responses, and thus reduced risk of allergic reactions. Moreover, non-biologically-derived hydrophilic polymers which are crosslinked in vivo offer the potential for formulations that are injected at low molecular weight and thus low viscosity, requiring low extrusion force for injection and making them straightforward to deploy to a patient using a thin gauge needle.

SUMMARY

In some aspects, the present disclosure pertains to injectable in vivo crosslinking materials for use as soft tissue fillers that comprise (a) a reactive multi-arm polymer that comprises a plurality of hydrophilic polymeric arms, at least a portion of the hydrophilic polymeric arms comprising one or more reactive end groups and (b) a multifunctional compound that comprises functional groups that are reactive with the reactive end groups of the reactive multi-arm polymer.

In some embodiments, which may be used in conjunction with these aspects, the hydrophilic polymeric arms may comprise one or more hydrophilic monomers.

In some embodiments, the hydrophilic polymeric arms may comprise one or more monomers selected from N-vinyl pyrrolidone, ethylene oxide, hydroxyethyl acrylate, hydroxyethyl methacrylate, PEG methyl ether acrylate or PEG methyl ether methacrylate.

In some embodiments, which may be used in conjunction with any of the above aspects and embodiments, the hydrophilic polymeric arms may further comprises a hydrolysable ester group.

In some embodiments, which may be used in conjunction with any of the above aspects and embodiments, the reactive end groups may be electrophilic groups and the functional groups may be nucleophilic groups.

In some embodiments, which may be used in conjunction with any of the above aspects and embodiments, the reactive end groups may be selected from N-hydroxysuccinimide esters, imidazole esters, imidizole carboxylates and benzotriazole esters.

In some embodiments, which may be used in conjunction with any of the above aspects and embodiments, the functional groups may be selected from amine groups and thiol groups.

In some embodiments, which may be used in conjunction with any of the above aspects and embodiments, the multifunctional compound may comprise a polyamine.

In some embodiments, which may be used in conjunction with any of the above aspects and embodiments, the reactive end groups of the reactive multi-arm polymer and the functional groups of the multifunctional compound react with one another via an amide coupling reaction. In some of these embodiments, the reactive end groups of the reactive multi-arm polymer comprise carboxyl groups, the functional groups of the multifunctional compound comprise amine groups, and the in vivo crosslinking material further comprises a carbodiimide coupling agent, such as 1-ethyl-3-(3-dimethylaminopropyl)carbodiimide (EDC) among others.

In other aspects, the present disclosure pertains to systems for forming injectable in vivo crosslinking materials in accordance with any of the above aspects and embodiments, which comprise (a) a first composition comprising the reactive multi-arm polymer and (b) a second composition comprising the multifunctional compound.

In some embodiments, the first composition, the second composition, or both the first composition and the second composition may comprise a therapeutic agent, an imaging agent, or both.

In some embodiments, which may be used in conjunction with any of the above aspects and embodiments, the system may comprise a first syringe barrel containing the first composition and a second first syringe barrel containing the second composition.

In some embodiments, which may be used in conjunction with any of the above aspects and embodiments, the system further comprises a delivery device configured to deliver a mixture of the first composition and the second composition into epidermis, dermis, and/or subcutaneous tissue of a patient. In some of these embodiments, the delivery device comprises a first reservoir containing the first composition and a second reservoir containing the second composition and/or the delivery device comprises a needle that is configured to inject the injectable in vivo crosslinking material into epidermis, dermis, and/or subcutaneous tissue of a patient.

In other aspects, the present disclosure pertains to methods comprising injecting an injectable in vivo crosslinking material in accordance with any of the above aspects and embodiments into epidermis, dermis, and/or subcutaneous tissue of a patient. Some of these embodiments, the injectable in vivo crosslinking material is injected beneath a skin defect that is lower or deeper than surrounding skin and/or thein vivo crosslinking material is molded by a healthcare within the patient after injection.

BRIEF DESCRIPTION OF THE DRAWINGS

FIG. 1 is a schematic illustration of a method of crosslinking a reactive multi-arm polymer with a multifunctional compound, in accordance with an embodiment of the present disclosure.

DETAILED DESCRIPTION

In various aspects, the present disclosure pertains to injectable in vivo crosslinking materials for use as soft tissue fillers, to compositions for forming such injectable in vivo crosslinking materials, and to methods of using such compositions.

In some embodiments, the injectable in vivo crosslinking materials of the present disclosure comprise a reactive multi-arm polymer, a multifunctional compound that comprises functional groups that are reactive with the reactive multi-arm polymer and, optionally, one or more additional agents such as therapeutic agents and/or contrast agents, among other possibilities.

The multi-arm polymers for use in the present disclosure comprise a plurality of polymeric arms (e.g., having two, three, four, five, six, seven, eight, nine, ten or more arms). At least a portion of the total polymeric arms in the injectable in vivo crosslinking material (e.g., ranging from 1% to 2.5% to 5% to 10% to 25% to 50% or 75% to 90% to 95% to 97.5% to 99% to 100% of the polymeric arms) comprise one or more reactive end groups.

In various embodiments, the polymeric arms are hydrophilic polymeric arms. Such hydrophilic polymeric arms which may be composed of any of a variety of synthetic, natural, or hybrid synthetic-natural polymers including, for example, poly(alkylene oxides) such as poly(ethylene oxide) (also referred to as PEG), poly(propylene oxide) or poly(ethylene oxide-co-propylene oxide), poly(vinylpyrrolidone), poly(vinyl alcohol), poly(allyl alcohol), poly(ethyleneimine), poly(allylamine), poly(vinyl amine), polyoxazolines including poly(2-alkyl-2-oxazolines) such as poly(2-methyl-2-oxazoline), poly(2-ethyl-2-oxazoline) and poly(2-propyl-2-oxazoline), poly(amino acids), polysaccharides, and combinations thereof.

In some embodiments, the polymeric arms extend from a core region. In certain of these embodiments, the core region comprises a residue of a polyol that is used to form the polymeric arms. Illustrative polyols may be selected, for example, from straight-chained, branched and cyclic aliphatic polyols including straight-chained, branched and cyclic polyhydroxyalkanes, straight-chained, branched and cyclic polyhydroxy ethers, including polyhydroxy polyethers, straight-chained, branched and cyclic polyhydroxyalkyl ethers, including polyhydroxyalkyl polyethers, straight-chained, branched and cyclic sugars and sugar alcohols, such as glycerol, mannitol, sorbitol, inositol, xylitol, quebrachitol, threitol, arabitol, erythritol, adonitol, dulcitol, fucose, ribose, arabinose, xylose, lyxose, rhamnose, galactose, glucose, fructose, sorbose, mannose, pyranose, altrose, talose, tagatose, pyranosides, sucrose, lactose, and maltose, oligomers (defined herein as ranging from two to ten units, including dimers, trimers, tetramers, pentamers, hexamers, heptamers, octamers, enneamers and decamers) of straight-chained, branched and cyclic sugars and sugar alcohols, polymers (defined herein as eleven or more units) of straight-chained, branched and cyclic sugars and sugar alcohols, including the preceding sugars and sugar alcohols, starches, amylose, dextrins, cyclodextrins, as well as polyhydroxy crown ethers, and polyhydroxyalkyl crown ethers.

Illustrative polyols also include aromatic polyols including 1,1,1-tris(4'-hydroxyphenyl) alkanes, such as 1,1,1-tris(4-hydroxyphenyl)ethane, and 2,6-bis(hydroxyalkyl)cresols, among others. In certain beneficial embodiments, the polyol is an oligomer of a sugar alcohol such as glycerol, mannitol, sorbitol, inositol, xylitol, or erythritol, among others. In certain beneficial embodiments, the polyol may contain three or more hydroxyl groups, for example, between four and twelve hydroxyl groups in certain cases.

In certain embodiments, the reactive end groups are selected from electrophilic groups and nucleophilic groups.

In certain embodiments, the reactive groups may be electrophilic groups selected from imidazole esters, imidazole carboxylates, benzotriazole esters, and imide esters, including N-hydroxysuccinimidyl esters. A particularly beneficial electrophilic reactive group is an N-hydroxysuccinimidyl ester group. In certain embodiments, the reactive groups may be nucleophilic groups selected from amine groups and/or thiol groups.

In particular embodiments, a reactive multi-arm polymer may be formed by reacting (a) a polymer that comprises a core (e.g., a polyol residue core, among others) and a plurality of polymeric arms, at least a portion of which are terminated in one or more hydroxyl groups with (b) a cyclic anhydride (e.g., glutaric anhydride, succinic anhydride, malonic anhydride, etc.) to form a reaction product in the form of a polymer that comprises the core and the plurality of polymeric arms, at least a portion of which polymeric arms are terminated in a moiety that comprises a carboxylic acid group and a hydrolysable ester group positioned between the carboxylic acid group and the polymeric arm. Subsequently, this reaction product may be treated with a coupling agent (e.g., a carbodiimide coupling agent such as N,N'-dicyclohexylcarbodiimide (DCC), 1-Ethyl-3-(3-dimethylaminopropyl)carbodiimide (EDC), N-Hydroxybenzotriazole (HOBt), BOP reagent, and/or another coupling agent) and N-hydroxysuccinimide (NHS), to yield a reactive multi-arm polymer comprising succinimidyl end groups, in particular, a reactive multi-arm polymer that comprises a core and a plurality of polymeric arms, at least a portion of which comprise a moiety that comprises a hydrolysable ester group and a succinimide ester group.

In some embodiments, the polymeric arms are formed by polymerization of at least one type of monomer from a suitable multifunctional initiator molecule. In some embodiments, the multifunctional initiator molecule may a polyol. In a particular embodiment, a polyol, specifically, a polyol having eight hydroxyl groups such as tripentaerythritol, may be used as an initiator for reaction in which a cyclic alkylene oxide, specifically, ethylene oxide, is polymerized in the presence of the polyol initiator and a catalyst, for example, a strong base such as butyl lithium or potassium t-butoxide, to form a polymer in which eight polyalkylene oxide arms extend from a polyol residue core. The terminal hydroxyl groups are then converted to succinimidyl glutarate groups using glutaric anhydride and N-hydroxysuccinide as reagents.

Using the above and innumerable other techniques, reactive multi-arm polymers (e.g., one having 2, 3, 4, 5, 6, 7, 8, 9, 10 or more arms) may be formed, which comprise a core and a plurality of hydrophilic polymeric arms extending from the core, wherein at least a first portion of the polymeric arms each comprises one or more reactive end groups.

Reactive multi-arm polymers in accordance with the present disclosure may be water soluble.

In various aspects, a reactive multi-arm polymer in accordance with the present disclosure may be combined with a suitable multifunctional compound to form a soft tissue filler that is crosslinkable in vivo.

In various embodiments, a reactive multi-arm polymer in accordance with the present disclosure may be crosslinked with a multifunctional compound having functional groups that are reactive with the reactive groups of the multi-arm polymer.

For example, in some embodiments, the functional groups of the multifunctional compound may be nucleophilic groups and the reactive groups of the multi-arm polymer may be electrophilic groups. In some embodiments, the functional groups of the multifunctional compound may be electrophilic groups and the reactive groups of the reactive multi-arm polymer may be nucleophilic groups.

In various embodiments, the reactive groups of the reactive multi-arm polymer and the functional groups of the multifunctional compound react with one another via an amide coupling reaction.

In certain embodiments, the functional groups of the multifunctional compound may be nucleophilic groups selected from amine groups and thiol groups. On the other hand, in certain embodiments, the functional groups of the multifunctional compound may be electrophilic groups selected from imidazole esters, imidazole carboxylates, benzotriazole esters, and imide esters, including N-hydroxysuccinimidyl esters.

In certain embodiments, the multifunctional compound may be a polyamine. Examples of polyamines suitable for use in the present disclosure include, for example, small molecule polyamines (e.g., containing at least two amine groups, for instance, from 3 to 20 amine groups, in some embodiments), comb polymers having amine side groups, and branched polymers having amine end groups, including dendritic polymers having amine end groups.

Particular examples of multifunctional amines which may be used as the multifunctional compound include trilysine, ethylenetriamine, diethylene triamine, hexamethylenetriiamine, di(heptamethylene) triamine, di(trimethylene) triamine, bis(hexamethylene) triamine, triethylene tetramine, tripropylene tetramine, tetraethylene pentamine, hexamethylene heptamine, pentaethylene hexamine, dimethyl octylamine, and dimethyl decylamine, and JEFFAMINE polyetheramines available from Huntsman Corporation, among others. Further particular examples of multifunctional amines include polypeptides including poly(L-lysine), chitosan, and poly(allyl amine), among others.

Other embodiments where the reactive groups of the reactive multi-arm polymer and the functional groups of the multifunctional compound react with one another via an amide coupling reaction are based on injectable in vivo crosslinking materials where the reactive multi-arm polymer comprises carboxyl end groups and the functional groups of the multifunctional compound are amine groups. For example, in some embodiments, the multi-arm polymers having hydrophilic polymeric arms that comprise carboxyl end groups can be reacted with a coupling agent, for example, a carbodiimide coupling agent such as 1-ethyl-3-(3-dimethylaminopropyl)carbodiimide (EDC) to form an O-acylisourea intermediate, which in turn reacts with amine groups to form amide linkages in vivo.

In various embodiments, injectable in vivo crosslinking materials for use as soft tissue fillers, are formed by combining a first composition comprising a reactive multi-arm polymer like that described above (e.g., a first fluid composition comprising the reactive multi-arm polymer or a first dry composition that comprises the multi-arm polymer, to which a suitable fluid such as water for injection, saline, etc. can be added to form a first fluid composition) and (b) a second composition comprising a multifunctional compound like that described above (e.g., a second fluid composition comprising the multifunctional compound, or a second dry composition that comprises the multifunctional compound, to which a suitable fluid such as water for injection, saline, etc. can be added to form a second fluid composition).

For example, as shown schematically in FIG. 1, a reactive multi-arm polymer 110 having a core 110c, arms 110a and reactive end groups 110e like that described herein (e.g., having a polyol residue core, hydrophilic polymeric arms, and reactive succinimidyl end-groups or reactive carboxyl end groups) may be crosslinked with a multifunctional compound 120 like that described herein (e.g., a polyamine such as trilysine) to form a crosslinked product 130.

In addition to the reactive multi-arm polymer, the first composition may further comprise, for example, additional agents such as therapeutic agents and/or contrast agents, among other possibilities. Likewise, in addition to the multifunctional compound, the second composition may further comprise, for example, additional agents such as therapeutic agents and/or contrast agents, among other possibilities.

In various embodiments, the injectable in vivo crosslinking materials for use as soft tissue fillers of the present disclosure may be delivered to the epidermis, dermis, and/or subcutaneous tissue (also called the hypodermis) of a patient a suitable delivery device. Alternatively, the injectable in vivo crosslinking materials may be used delivered in or between organs.

In some embodiments, the delivery device may include a needle, one or more reservoirs (e.g., one or more syringe barrels), and one or more actuators for expelling the contents of the one or more reservoirs (e.g., one or more plungers).

For example, the delivery device may comprise a first reservoir that contains a first fluid composition comprising a reactive multi-arm polymer like that described above (or a first dry composition to which a suitable fluid can be added to form a first fluid composition) and a second reservoir that contains a second fluid composition comprising a multifunctional compound like that described above (or a second dry composition to which a suitable fluid such as water for injection, saline, etc. can be added to form the second fluid composition). During operation, the first and second fluid compositions are dispensed from the first and second reservoirs, whereupon the first and second fluid compositions interact and crosslink with one another.

In certain embodiments, the system may include a delivery device that comprises a double-barrel syringe, which includes first barrel having a first barrel outlet containing the first composition, a second barrel having a second barrel outlet containing the second composition, a first plunger that is movable in the first barrel, and a second plunger that is movable in the second barrel.

In certain embodiments, the device may further comprise a mixing section having a first mixing section inlet in fluid communication with the first reservoir (e.g., in fluid communication with the first barrel outlet), a second mixing section inlet in fluid communication with second reservoir (e.g., in fluid communication with the second barrel outlet), and a mixing section outlet in fluid communication with a needle.

During operation, when the first and second plungers are depressed, the first and second fluid compositions are dispensed from the first and second barrels, whereupon the first and second fluid compositions interact and form an injectable material, which is administered tissue of a subject, and which subsequently crosslinks in vivo to act as a soft tissue filler. For example, the first and second fluid compositions may pass from the first and second barrels, into the mixing section via first and second mixing section inlets, whereupon the first and second fluid compositions are mixed to form an admixture, which admixture exits the mixing section via the mixing section outlet and enters a needle, from which the admixture can be injected into a patient.

In additional aspects, the present disclosure pertains to crosslinked products that are implanted in tissue, in particular, crosslinked products of (a) a reactive multi-arm polymer as described herein and (b) a multifunctional compound as described herein, which are implanted in one or more of epidermis, dermis, or subcutaneous tissue.

As noted above, injectable in vivo crosslinking materials for use as soft tissue fillers in accordance with the present disclosure may be formed by mixing a first fluid composition comprising a reactive multi-arm polymer as described herein with a second composition comprising a multifunctional compound as described herein and injecting the mixture into one or more of epidermis, dermis, or subcutaneous tissue. Alternatively, the injectable in vivo crosslinking materials may be formed by mixing a first fluid composition comprising a reactive multi-arm polymer as described herein with a second composition comprising a multifunctional compound as described herein and injecting the mixture into or between organs.

In certain embodiments, the crosslinking rate of the mixture may be tuned to allow a healthcare provider who is administering the compositions sufficient time to mold the mixture after it is injected, thereby maximizing the aesthetic effect of the mixture, before the mixture crosslinks to a point where further molding of the mixture is prevented. For example, a crosslinking rate of the mixture may be such that the mixture is moldable for several minutes after the mixture is formed, after which further molding is prevented due to the degree of crosslinking that has occurred. The rate of crosslinking may be controlled through control of pH, for example, using suitable pH buffers, among other approaches.

The extent of crosslinking for a given material can be assessed, for example, by monitoring changes in the elastic modulus of the material, which can be measured using a rheometer can be used. In this regard, dynamic mechanical analysis can be used to measure the storage modulus (G') and the loss modulus (G") of a given material as a function of time and the variation of G' and G" in time can indicate the extent of the curing reaction. In certain embodiments, the crosslinking rate of the mixture can be such that an onset of cure occurs within a time period ranging from 1 minute to 10 minutes and/or such that full cure (e.g., 95% of the final stiffness) is achieved within a time period ranging from 30 minutes to 1 hour, among other possibilities.

Injectable in vivo crosslinking materials for use as soft tissue fillers as described herein (as well as first compositions comprising multi-arm polymer described herein and second compositions comprising multifunctional compounds described herein, which are combined to form the injectable in vivo crosslinking materials) may contain one or more additional agents.

Examples of such additional agents include therapeutic agents and imaging agents, among others.

Examples of imaging agents include (a) fluorescent dyes such as fluorescein, indocyanine green, or fluorescent proteins (e.g. green, blue, cyan fluorescent proteins), (b) contrast agents for use in conjunction with magnetic resonance imaging (MRI), including contrast agents that contain elements that form paramagnetic ions, such as $Gd^{(III)}$, $Mn^{(II)}$, $Fe^{(III)}$ and compounds (including chelates) containing the same, such as gadolinium ion chelated with diethylenetriaminepentaacetic acid, (c) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), (d) contrast agents for use in connection with x-ray fluoroscopy, including metals and metal compounds (e.g., metal salts, metal oxides, etc.), for instance, barium compounds, bismuth compounds and tungsten, among others, and iodinated compounds, among others, (e) radiocontrast agents, such as those based on the clinically important isotope $^{99m}Tc$, as well as other gamma emitters such as $^{123}I$, $^{125}I$, $^{131}I$, $^{111}In$, $^{57}Co$, $^{153}Sm$, $^{133}Xe$, $^{51}Cr$, $^{81m}Kr$, $^{201}Tl$, $^{67}Ga$, and $^{75}Se$, among others, (f) positron emitters, such as $^{18}F$, $^{11}C$, $^{13}N$, $^{15}O$, and $^{68}Ga$, among others, may be employed to yield functionalized radiotracer coatings, and (g) contrast agents for use in connection with near-infrared (NIR) imaging, which can be selected to impart near-infrared fluorescence to the coatings of the present disclosure, allowing for deep tissue imaging and device marking, for instance, NIR-sensitive nanoparticles such as gold nanoshells, carbon nanotubes (e.g., nanotubes derivatized with hydroxyl or carboxyl groups, for instance, partially oxidized carbon nanotubes), dye-containing nanoparticles, such as dye-doped nanofibers and dye-encapsulating nanoparticles, and semiconductor quantum dots, among others. NIR-sensitive dyes include cyanine dyes, squaraines, phthalocyanines, porphyrin derivatives and borondipyrromethane (BODIPY) analogs, among others.

Variations, modifications, and other implementations of the present disclosure in addition to the various embodiments described herein will occur to those of ordinary skill in the art. Accordingly, the present disclosure is not to be limited by the preceding illustrative description.

What is claimed is:

1. An injectable in vivo crosslinking material for use as soft tissue filler comprising (a) a reactive multi-arm polymer that comprises a plurality of hydrophilic polymeric arms, the hydrophilic polymer arms comprising poly(2-methyl-2-oxazoline) arms, at least a portion of the hydrophilic polymeric arms comprising one or more reactive end groups and (b) a multifunctional compound that comprises functional groups that are reactive with the reactive end groups of the reactive multi-arm polymer.

2. The injectable in vivo crosslinking material of claim 1, wherein the hydrophilic polymeric arms further comprises a hydrolysable ester group.

3. The injectable in vivo crosslinking material of claim 1, wherein the reactive end groups are electrophilic groups and the functional groups are nucleophilic groups.

4. The injectable in vivo crosslinking material of claim 1, wherein the reactive end groups are selected from N-hydroxysuccinimide esters, imidazole esters, imidizole carboxylates and benzotriazole esters.

5. The injectable in vivo crosslinking material of claim 1, wherein the functional groups are selected from amine groups and thiol groups.

6. The injectable in vivo crosslinking material of claim 1, wherein the multifunctional compound comprises a polyamine.

7. The injectable in vivo crosslinking material of claim 1, wherein the reactive end groups of the reactive multi-arm polymer and the functional groups of the multifunctional compound react with one another via an amide coupling reaction.

8. The injectable in vivo crosslinking material of claim 7, wherein the reactive end groups of the reactive multi-arm polymer comprise carboxyl groups, wherein the functional groups of the multifunctional compound comprise amine groups, and wherein the injectable in vivo crosslinking material further comprises a carbodiimide coupling agent.

9. The injectable in vivo crosslinking material of claim 1, wherein the injectable in vivo crosslinking material is moldable in situ.

10. A system for forming the injectable in vivo crosslinking material in accordance with claim 1, comprising (a) a first composition comprising the reactive multi-arm polymer and (b) a second composition comprising the multifunctional compound.

11. The system of claim 10 wherein the first composition, the second composition, or both the first composition and the second composition comprise a therapeutic agent, an imaging agent, or both.

12. The system of claim 10, comprising a first syringe barrel containing the first composition and a second first syringe barrel containing the second composition.

13. The system of claim 10, further comprising a delivery device configured to deliver a mixture of the first composition and the second composition into epidermis, dermis, and/or subcutaneous tissue of a patient.

14. The system of claim 13, wherein the delivery device comprises a first reservoir containing the first composition, a second reservoir containing the second composition, and a needle that is configured to inject the injectable in vivo crosslinking material into epidermis, dermis, and/or subcutaneous tissue of a patient.

15. The system of claim 13, wherein the injectable in vivo crosslinking material is moldable in situ.

16. A method comprising injecting the injectable in vivo crosslinking material in accordance with claim 1 into epidermis, dermis, and/or subcutaneous tissue of a patient.

17. The method of claim 16, wherein the injectable in vivo crosslinking material is injected beneath a skin defect that is lower or deeper than surrounding skin.

18. The method of claim 16, wherein in vivo crosslinking material is molded by a healthcare provider within the patient after injection.

* * * * *